US008178666B2

(12) United States Patent
Cioffi

(10) Patent No.: US 8,178,666 B2
(45) Date of Patent: May 15, 2012

(54) 2-AMINOBENZOXAZOLE PROCESS

(75) Inventor: Christopher Cioffi, Troy, NY (US)

(73) Assignee: Albany Molecular Research, Inc., Albany, NY (US)

(*) Notice: Subject to any disclaimer, the term of this patent is extended or adjusted under 35 U.S.C. 154(b) by 280 days.

(21) Appl. No.: 12/604,491

(22) Filed: Oct. 23, 2009

(65) Prior Publication Data

US 2010/0113772 A1 May 6, 2010

Related U.S. Application Data

(60) Provisional application No. 61/107,787, filed on Oct. 23, 2008.

(51) Int. Cl.
C07D 413/04 (2006.01)

(52) U.S. Cl. ........................................ 540/575; 544/368

(58) Field of Classification Search .................... None
See application file for complete search history.

(56) References Cited

U.S. PATENT DOCUMENTS

| 7,045,516 B1 | 5/2006 | Shiokawa et al. |
| 2003/0109714 A1 | 6/2003 | Wishart et al. |
| 2008/0045512 A1 | 2/2008 | Duplantier et al. |

FOREIGN PATENT DOCUMENTS

| WO | 9840381 A1 | 9/1998 |
| WO | 02076960 A1 | 10/2002 |
| WO | 02079753 A2 | 10/2002 |
| WO | 2008008518 A1 | 1/2008 |
| WO | 2008/019372 A2 | 2/2008 |

OTHER PUBLICATIONS

Chang et al., "Facile Synthesis of 2-Substituted Aminobenzoxazole. One Pot Cyclodesulfurization of N-(2-Hydroxyphenyl)-N' - phenylthioureas with Superoxide Radical Anion." Chemical Letters, The Chemical Society of Japan, 1986, pp. 1291-1294.
Ogura et al., "Studies on Heterocyclic Compounds. XXXIV[1]. Synthesis of 2-Substituted Aminobenzoxazoles with Nickel Peroxide." Chem. Pharm. Bull., vol. 29, 1981, pp. 1518-1524.
Katsura et al., "Studies on Antiulcer Drugs. III. [1]" Synthesis and Antiulcer Activities of Imidazol [1,2-α] pyridinylethylbenzoxazoles and Related Compounds. A Novel Class of Histamine $H_2$-Receptor Antagonists." Chem. Pharm. Bull., vol. 40, No. 6, 1992, pp. 1424-1438.
Whitman et al., "Discovery of a Potent, CNS-Penetrant Orexin Receptor Antagonist Based on an N,N-Disubstituted-1, 4-diazepane Scaffold that Promotes Sleep in Rats." ChemMedChem., vol. 4, 2009, pp. 1069-1074.
Webb et al., "Diphenyl Cyancarbonimidate and Dichlorodiphenoxymethane as Synthons for the Construction of Heterocyclic Systems of Medicinal Interest." J. Heterocyclic Chem., vol. 24, Jan.-Feb. 1987, pp. 275-278.
Garín et al., "Diheterocyclic Compounds from Dithiocarbamates and Derivatives Thereof. I. 2,2"—(Arylenediamino)bisbenzoazoles, 2,2"-(Arylenediamino)bis(imidazopyridines) and 8,8"— (Arylenediamino)bispurines" J. Heterocyclic Chem., vol. 27, 1990, pp. 221-226.
El-Faham et al., "Chloroformamidinium Salts: Efficient Reagents for Preparation of 2-Aminobenzoimidazole, 2-Aminobenzoxazole, and 2-Aminobenzothiazole Derivatives." J. Heterocyclic Chem., vol. 43, May-Jun. 2006, pp. 599-606.
Sato, et al., "Benzoxazole Derivatives as Novel 5-$HT_3$ Receptor Partial Agonists in the Gut." American Chemical Society., 1998, pp. 3015-3021.
Yoshida et al., Orally Active Benzoxazole Derivative as 5-$HT_3$ Receptor Partial Agonist for Treatment of Diarrhea-Predominant Irritable Bowel Syndrome., Journal of Medicinal Chemistry, Mar. 8, 2005, pp. A-E.
O'Donnell et al., "Discovery of 4-(5-Methyloxazolo[4,5-b]pyridine-2-yl)-1,4-diazabicyclo[3.2.2]nonane (CP-810,123), a Novel α7 Nicotinic Acetylcholine Receptor Agonist for the Treatment of Cognitive Disorders in Schizophrenia: Synthesis, SAR Development, and in Vivo Efficacy in Cognition Models.", Journal of Medicinal Chemistry, Dec. 31, 2009, pp. 1222-1237.
Hetzheim et al., "Synthese substituierter 2-Amino-benzoxazole.", Pharmazie, vol. 42, 1987, pp. 80-82.
Garín et al., "Chemoselectivity in the Oxidation of Unsymmetrical Thioureas with NBS/Sulfuric Acid: Benzothiazoles VS. 1,2,4-Thiadiazoles.", Synthetic Communications, vol. 20(15), 1990, pp. 2327-2334.
Haake et al., "Diphenyl N-Sulfamoylcarbonimidate—A Versatile Building Block in Heterocyclic Synthesis.", Synthesis, Sep. 1991, pp. 753-758.
Kövér et al., "Novel and Efficient Synthesis of 6-Chloro-2-(substituted amino)benzoxazoles.", Synthesis,19,Jun. 2, 1994, Jul. 18, 1994, and Nov. 1994, pp. 1124-1126.
Perkins et al., "Synthesis of 2-(Alkylamino)benzimidazoles.", Tetrahedron Letters, Elsevier Science Ltd., 1999, pp. 1103-1106.
Tian et al., "A general synthesis of N-aryl- and N-alkyl-2aminobenzoxazoles", Tetrahedron Letters, Elsevier Science Ltd., 46, 2005, pp. 8341-8343.
Heinelt et al., "A convenient method from the synthesis of 2-amino substituted aza-heterocycles from $N,N^1$—disubstituted thioureas using TsCl/NaOH.", Tetrahedron Letters, Elsevier Science Ltd., 60, 2004, pp. 9883-9888.
International Search Report for PCT/US2009/061855, mailed Jan. 22, 2010.
Webb, R. L. et al., "Diphenyl cyancarbonimidate and dichlorodiphenoxymethane as synthons for the construction of heterocyclic systems of medicinal interest," Journal of Heterocyclic Chemistry, vol. 24, No. 1, pp. 275-278, 1987.
Webb, R.L., Labaw, C. S., "Diphenyl cyanocarbonimidate. A versatile synthon for the construction of heterocyclic systems," Journal of Heterocyclic Chemistry, vol. 19, No. 5, pp. 1205-1206, 1982.

(Continued)

Primary Examiner — Kamal Saeed
(74) Attorney, Agent, or Firm — Heslin Rothenberg Farley & Mesiti P.C.

(57) ABSTRACT

A method for forming an optionally substituted 2-aminobenzoxazole compound includes: contacting an optionally substituted 2-aminophenol compound with (1) an amine of the formula $NHR^2R^3$, wherein $R^2$ and $R^3$ are each independently selected from H, an optionally substituted alkyl group or an optionally substituted aryl group, or $R^2$ and $R^3$, taken together with the nitrogen atom to which they are attached, form an optionally substituted heterocyclic ring; and (2) a reactant selected from the group consisting of: (a) $C(OR)_4$, wherein R represents an alkyl group; (b) $C(OAr)_4$, wherein Ar represents an aryl group; and (c) $CCl_2(OAr)_2$, wherein Ar represents an aryl group, in combination with a base; thereby forming the optionally substituted 2-aminobenzoxazole compound.

19 Claims, No Drawings

OTHER PUBLICATIONS

Haake, M. et al., "Diphenyl N-Sulfamozlcarbonimidate—A Versatile Building Block in Heterocyclic Synthesis," *Synthesis*, Georg Thieme Verlag, Stuttgart, DE, No. 7, pp. 753-758, ISSN: 0039-7881, 1991.

Tian, Z. et al., "A general synthesis of N-aryl and N-alkyl-2-aminobenzoxazoles," *Tetrahedron Letters*, Elsevier, Amsterdam, NL, vol. 46, No. 48, pp. 8341-8343, ISSN: 0040-4039, 2005.

Sato, Y. et al., "Benzoxazole Derivatives as Novel 5-HT3 Receptor Partial Agonists in the Gut," *Journal of Medicinal Chemistry*, American Chemical Society, Washington, US, pp. 3015-3021, ISSN: 0022-2623, 1998.

Kantlehner, W. et al., "Orthoamide, XXXVIII. Beitraureestern und Trialkoxyacetonitrilen," *Liebigs Annalen Der Chemie*, No. 3, pp. 507-529, XP002562034, 1982.

2-AMINOBENZOXAZOLE PROCESS

CROSS-REFERENCE TO RELATED APPLICATION

This application claims the benefit of priority from U.S. Provisional Patent Application Ser. No. 61/107,787, filed Oct. 23, 2008, the disclosure of which is incorporated herein by reference.

FIELD OF THE INVENTION

The present invention generally relates to aminobenzoxazole compounds and more particularly to a convenient method for synthesizing 2-aminobenzoxazoles.

BACKGROUND OF THE INVENTION

Substituted 2-aminobenzoxazoles are ubiquitous scaffolds featured in a wide variety of therapeutic agents or as key intermediates in the synthesis of therapeutic agents. Such agents include; dopamine antagonists, 5-HT$_3$ partial agonists, TIE-2 inhibitors, FKBP inhibitors, IMPDH inhibitors, PPARα and PPARγ antagonists, HIV reverse transcriptase inhibitors, leukotriene biosynthesis inhibitors, bombesin receptor antagonists, intergrin receptor ligands, platelet ADP receptor ligands, CCR3 receptor antagonists, fungicides, sedatives, and muscle relaxants.

Known methods for preparing substituted 2-aminobenzoxazoles include cyclodesulfurization, which involves the cyclization of a thiourea under oxidative conditions. (cf. *J. Heterocyclic Chem.* 1990, 27, 221; *Tetrahedron Lett.* 1999, 40, 1103; *Chem. Pharm. Bull.* 1981, 29, 1518; *Chem. Lett.* 1986, 8, 1291; WO9840381-A1; *Chem. Pharm. Bull.* 1992, 40, 1424) The thiourea is typically generated by reacting an aminophenol with a thioisocyanate. In many of the reported examples, a toxic metal oxide, e.g. HgO, PbO, or a potentially explosive oxidant, e.g. NaOCl, K$_2$O, is employed.

Another method for synthesizing 2-aminobenzoxazole compounds involves the nucleophilic displacement reaction of a 2-substituted benzoxazole, wherein the 2-substituent may be sulfur, thiomethyl, halogen or phenoxide, with an amine. (cf. *J. Med. Chem.* 1998, 41, 3015; *Synthesis,* 1994, 1124; *Pharmazie,* 1997, 52, 585) Such methods typically require the use of a scrubber system to oxidize generated methanethiol or hydrogen sulfide, or a reactive reagent such as phosphorous oxychloride to form the 2-chlorobenzoxazole intermediate.

Several procedures have been reported wherein a substituted 2-aminobenzoxazole can be produced directly from a 2-aminophenol. (*Synth. Commun.* 1990, 20, 2327; *J. Heterocyclic Chem.* 1987, 24, 275; *Synthesis,* 1991, 753; *J. Heterocyclic Chem.* 2006, 43, 599; *Tetrahedron,* 2004, 60, 9883) Such methods, which involve an imidate and thioimidate based reagent, iminium salts, cyanogen bromide, or 1,1-diimidazoleimine, require the formation of the imidate or salt prior to cyclization, and may further entail the use of hazardous reagents or elaborate purification procedures.

A process for preparing substituted 2-aminobenzoxazoles from 2-aminophenols and thioisocyanates with transition metals is described in US Pat. Appl. Serial No. 20030109714-A1, the disclosure of which is incorporated herein by reference. In a further elaboration of this method, substituted 2-aminobenzoxazoles are prepared from 2-aminophenols and thioisocyanates via an oxidative desulfurization utilizing hydrogen peroxide and lithium hydroxide. (cf. *Tet. Lett,* 2005, 46, 8341)

A method for constructing a variety of substituted 2-aminobenzoxazoles that is convenient, efficient, versatile, and amenable to large-scale production would be highly desirable. Such a method is realized in the present invention.

SUMMARY OF THE INVENTION

The present invention is directed to a method for forming an optionally substituted 2-aminobenzoxazole compound that comprises: contacting an optionally substituted 2-aminophenol compound with (1) an amine of the formula NHR$^2$R$^3$, wherein R$^2$ and R$^3$ are each independently selected from H, an optionally substituted alkyl group or an optionally substituted aryl group, or R$^2$ and R$^3$, taken together with the nitrogen atom to which they are attached, form an optionally substituted heterocyclic ring; and (2) a reactant selected from the group consisting of: (a) C(OR)$_4$, wherein R represents an alkyl group; (b) C(OAr)$_4$, wherein Ar represents an aryl group; and (c) CCl$_2$(OAr)$_2$, wherein Ar represents an aryl group, in combination with a base; thereby forming the optionally substituted 2-aminobenzoxazole compound.

The method of the present invention provides for the synthesis of substituted 2-aminobenzoxazoles from a variety of amines and 2-aminophenols by a convenient one-pot procedure, using a tetraalkyl or tetraarylorthocarbonate compound, or a 1,1-dichlorodiaryloxymethane compound. Several such compounds, for example, tetramethyl or tetraethyl orthocarbonate and 1,1-dichlorodiphenoxymethane, are commercially available.

DETAILED DESCRIPTION OF THE INVENTION

As shown in Scheme 1 below, the desired 2-aminobenzoxazole compounds can be produced by the reaction of an amine with a 2-aminophenol compound in the presence of either a tetraalkyl or tetraaryl orthocarbonate, or a 1,1-dichlorodiaryloxymethane in combination with a base. The reagents are readily available and easily handled, and the reaction conditions are mild. Typically, the reaction is carried out at normal room temperature, but in some cases an increase in temperature to as high as about 80° C. is beneficial. The reaction by-products are relatively benign, particularly by comparison with those produced by the previously known methods described above.

Scheme 1

Method Utilizing Tetramethyl orthocarbonate

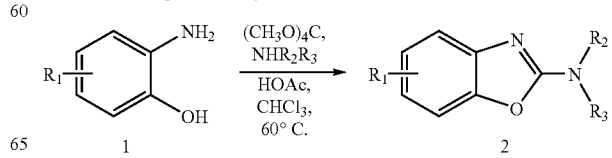

-continued
Method Utilizing 1,1-Dichlorodiphenoxymethane

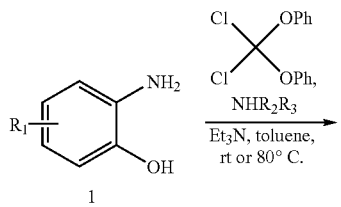

1

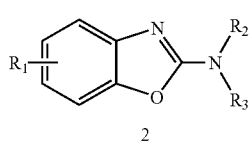

2

Method Using Tetramethyl Orthocarbonate

In accordance with the invention, substituted 2-aminobenzoxazoles can be prepared in one pot using commercially available tetramethyl orthocarbonate (2 eq, Aldrich), an amine (2 eq), and an optionally substituted 2-aminophenol (1 eq). The reaction may be carried out in the presence of acetic acid (4 eq) in chloroform at 60° C. (using a sealed tube for volatile amines). Tetramethyl orthocarbonate can be successfully replaced by its tetraethyl analogue in this reaction. Other useful solvents for the reaction include methanol, ethanol, isopropyl alcohol, acetonitrile, tetrahydrofuran, ethyl acetate, toluene, and combinations thereof.

The mild reaction conditions permit the reaction to be applied to compounds with sensitive functional groups, for example, esters. The reaction is clean, providing virtually spot-to-spot conversion from an aminophenol to a 2-methoxybenzoxazole to a 2-aminobenzoxazole. The work-up and purification is straightforward and easy; in many cases, a simple re-crystallization may be sufficient for purification of final compounds. The reaction is versatile, as is demonstrated by the variety of amine reactants listed in TABLE 1. As shown by the structures included in TABLE 2, electron donating and withdrawing substituents on the 2-aminophenol are also well tolerated.

The reaction by-products are methanol and, optionally, acetic acid. A simplified work-up may only involve concentration under reduced pressure, which makes the reaction particularly amenable to large-scale production. The reaction can be carried out in a variety of solvents, including methanol, acetonitrile, tetrahydrofuran, ethyl acetate, and toluene. Optionally, the solvent may include an acid such as acetic acid. However the reaction proceeds in good yield in chloroform without acetic acid.

Method Using 1,1-dichlorodiphenoxymethane

The synthesis of substituted 2-aminobenzoxazoles can be readily achieved by a versatile one-pot procedure utilizing 1,1-dichlorodiphenoxymethane, a primary or secondary amine, a base, and an optionally substituted 2-aminophenol. The base is preferably a tertiary amine (e.g. triethylamine, diisopropylethylamine, N-methylmorpholine, diazabicyclooctane, diazabicycloundecene, or an aromatic nitrogen heterocycle, e.g. pyridine. 1,1-Dichlorodiphenoxymethane is an easily handled crystalline solid. Preferably, the reaction is carried out in the presence of triethylamine in toluene at room temperature, providing the desired substituted 2-aminobenzoxazoles in acceptable to excellent yields. A mixture of 2-aminophenol (1 mmol), amine (1 mmol), 1,1-dichlorodiphenoxymethane (1 mmol), and triethylamine (2 mmol) in toluene (0.25 M) is stirred at temperature ranging from room ambient up to about 60° C. for up to about 16 hours. The mixture is washed sequentially with 1 N sodium hydroxide, 1 N hydrochloric acid and brine, dried over sodium sulfate, and filtered. The filtrate is concentrated under reduced pressure, and silica gel chromatography of the concentrate is performed with a Teledyne ISCO CombiFlash Companion unit.

As shown in TABLES 3 and 4, a variety of amines and substituted 2-aminophenols can be employed in this reaction. The reaction conditions are very mild; thus sensitive functional groups were well tolerated. The reaction is clean, providing virtually spot-to-spot conversion from a 2-aminophenol to a 2-phenoxybenzoxazole to a 2-aminobenzoxazole. The work-up and purification is straightforward and easy, in many cases, a simple re-crystallization being sufficient for purification of final compounds. The reaction by-products are phenol and triethylamine hydrochloride.

In one embodiment of the present invention, at least one of $R^2$ and $R^3$ comprises an alkyl group. In another embodiment, $R^2$ and $R^3$ together comprise an alkylene group. In other embodiments, the amine may comprise a primary amine, a cycloalkyl secondary amine, or a heterocyclic secondary amine. For optionally substituted arylamine reactants, the optionally substituted aryl group may comprise substituents selected from alkyl, aryl, heteroaryl, halo, alkoxy, hydroxyl, acyl, carboalkoxy, carboxy, nitro, and combinations thereof.

Synthesis of 5-Chloro-7-methyl-2-(4-methyl-1,4-diazepan-1-yl)benzo[d]oxazole

The usefulness of the method of the present invention was demonstrated by employing it for the synthesis of the 5-HT$_3$ partial agonist 5-chloro-7-methyl-2-(4-methyl-1,4-diazepan-1-yl)benzo[d]oxazole (6) (Meiji Seika, Ltd.). This compound is currently in Phase I clinical trials for the treatment of diarrhea predominant irritable bowel syndrome (IBS-D). (cf. U.S. Pat. No. 7,045,516 and references cited within; *J. Med. Chem.* 1998, 41, 3015; *J. Med. Chem.* 2005, 48, 7075)

The method of the invention, shown in Scheme 2 utilizing tetramethyl orthocarbonate, produced the desired compound in excellent yield (1.68 gram scale) and in fewer steps than the prior art procedure, also shown in Scheme 2 below.

The method of the invention is superior to the prior art synthesis procedure in several important respects: 1) it is economical in terms of fewer required steps; 2) it is safer; avoiding the use of toxic and highly flammable carbon disulfide or highly reactive phosphorous pentachloride; 3) the by-products (methanol, acetic acid) are benign relative to hydrogen sulfide gas, which requires a scrubber system for large scale preparations; 4) the reaction conditions are milder, the reaction being heated at 60° C. rather than at the reflux temperature of toluene. Solvents other than chloroform can be used, and purification of the product by recrystallization instead of column chromatography is generally feasible.

Scheme 2

Current Method For Generating 5-chloro-7-methyl-2-(4-methyl-1,4-diazepan-1-yl)benzo[d]oxazole

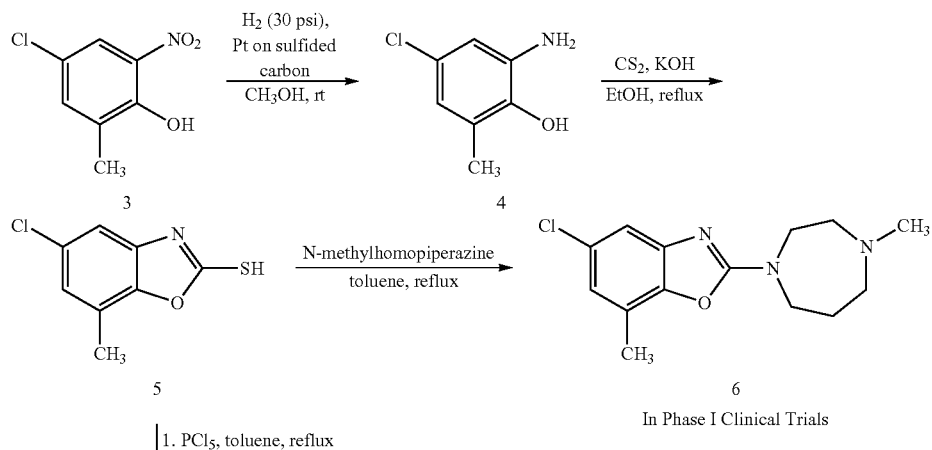

In Phase I Clinical Trials

Method Utilizing Tetramethyl Orthocarbonate

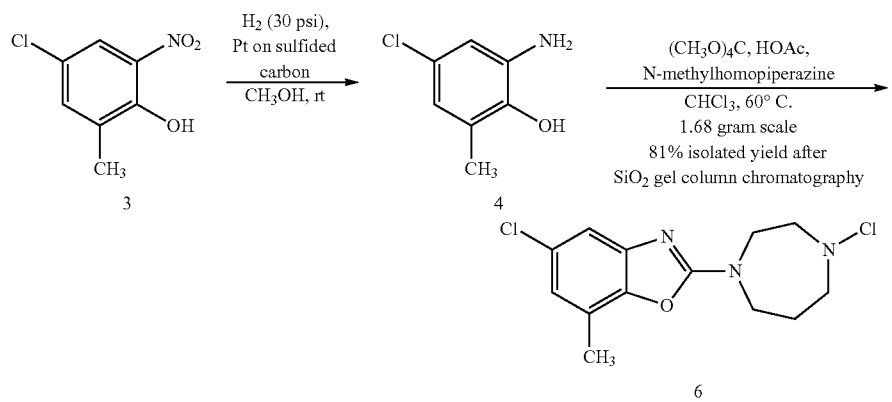

| TABLE 1 |
|---|
| Tetramethyl Orthocarbonate Method With Various Amines |

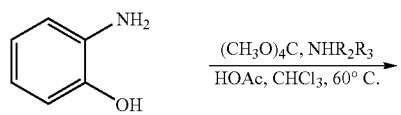

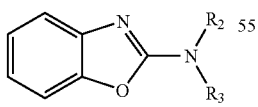

| Entry | Amine | % Yield |
|---|---|---|
| 1 | NBoc-piperazine | >99 |

| TABLE 1-continued |
|---|
| Tetramethyl Orthocarbonate Method With Various Amines |

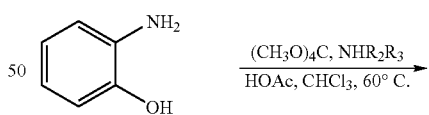

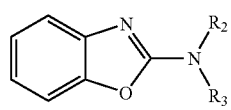

| Entry | Amine | % Yield |
|---|---|---|
| 2 | morpholine | 69 |

TABLE 1-continued

Tetramethyl Orthocarbonate Method With Various Amines

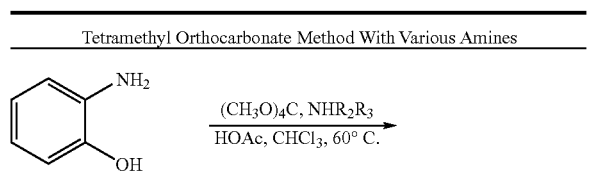

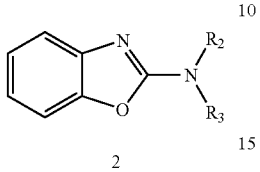

| Entry | Amine | % Yield |
|---|---|---|
| 3 | piperidine | 88 |
| 4 | pyrrolidine | 90 |
| 5 | azepane (hexamethyleneimine) | 72 |
| 6 | N-methylbenzylamine | 65 |
| 7 | 2-methylpiperidine | 32 |
| 8 | proline methyl ester | 63 |
| 9 | 4-phenylpiperidine | 50 |
| 10 | aniline | 73 |
| 11 | cyclopropylamine | 64 |
| 12 | tert-butylamine | 36 |
| 13 | allylamine | 69 |
| 14 | phenethylamine | 69 |
| 15 | benzylamine | 47 |
| 16 | isopropylamine | 38 |
| 17 | NH₃ (0.5 M/dioxane)ᵃ | 37 |
| 18 | cyclohexylamine | 43 |

2-Aminophenol was used in all cases. Isolated yield after column chromatography (most yields are for two runs).
ᵃ 0.5 M NH$_3$ in 1,4-dioxane used as solvent and the experiment was conducted in a sealed tube.

TABLE 2

Tetramethyl Orthocarbonate Method With Substituted 2-Aminophenols

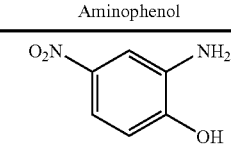

| Entry | Aminophenol | % Yield |
|---|---|---|
| 1 | 4-nitro-2-aminophenol | 83 |

TABLE 2-continued

Tetramethyl Orthocarbonate Method With Substituted 2-Aminophenols

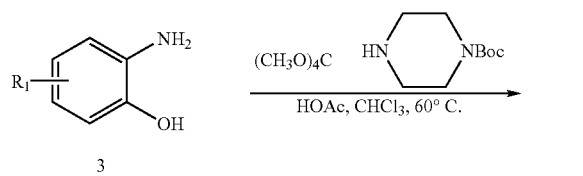

3

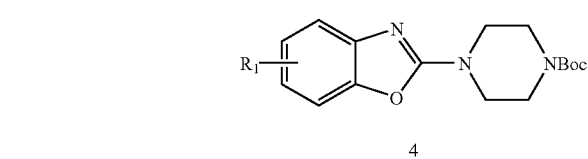

4

| Entry | Aminophenol | % Yield |
|---|---|---|
| 2 | 4-Cl-2-aminophenol | >99 |
| 3 | 4-methoxy-2-aminophenol | 50 |
| 4 | 4-methyl-2-aminophenol | 94 |
| 5 | 3-amino-2-naphthol | 95 |
| 6 | 4-F-2-aminophenol | 88 |
| 7 | 4-phenyl-2-aminophenol | 63 |
| 8 | 3-Br-2-aminophenol | 35 |
| 9 | methyl 3-amino-2-hydroxybenzoate | 18 |

TABLE 2-continued

Tetramethyl Orthocarbonate Method With Substituted 2-Aminophenols

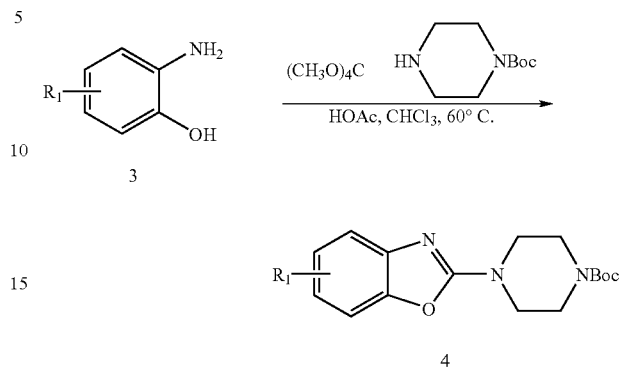

| Entry | Aminophenol | % Yield |
|---|---|---|
| 10 | 4-amino-1,3-dihydroxybenzene | 32 |

N-Boc-piperazine was used in all cases. Yields shown represent isolated yields following column chromatography.

TABLE 3

1,1-Dichlorodiphenoxymethane Method With Various Amines

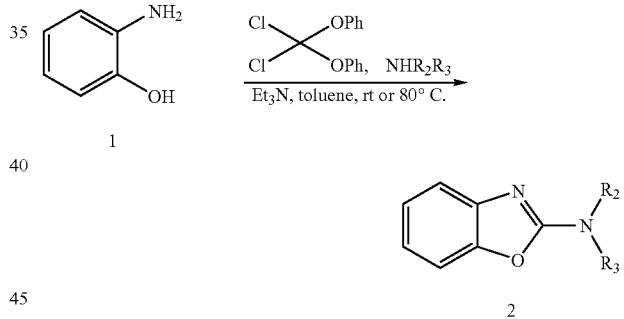

| Entry | Amine | % Yield |
|---|---|---|
| 1 | N-Boc-piperazine | 92 |
| 2 | morpholine | 71 |
| 3 | piperidine | 85 |

TABLE 3-continued

1,1-Dichlorodiphenoxymethane Method With Various Amines

| Entry | Amine | % Yield |
|---|---|---|
| 4 | pyrrolidine | 89 |
| 5 | azepane (hexamethyleneimine) | 58 |
| 6 | 1-methyl-1,4-diazepane | 91 |
| 7 | N-methylbenzylamine | 75 |
| 8 | 4-phenylpiperidine | 67 |
| 9 | aniline | 40 |
| 10 | allylamine | 51 |
| 11 | benzylamine | 69 |

2-Aminophenol was used in all cases. Yields shown represent isolated yields following column chromatography.

TABLE 4

1,1-Dichlorodiphenoxymethane Method With Substituted 2-Aminophenols

| Entry | Aminophenol | % Yield |
|---|---|---|
| 1 | 4-nitro-2-aminophenol ($O_2N$, $NH_2$, $OH$) | 80 |
| 2 | 4-chloro-2-aminophenol (Cl, $NH_2$, OH) | 96 |
| 3 | 4-methoxy-2-aminophenol ($H_3CO$, $NH_2$, OH) | 40 |
| 4 | 4-methyl-2-aminophenol ($H_3C$, $NH_2$, OH) | >99 |
| 5 | 5-phenyl-2-aminophenol (biphenyl, $NH_2$, OH) | 43 |
| 6 | methyl 3-amino-2-hydroxybenzoate ($CO_2CH_3$, $NH_2$, OH) | 75 |

N-Boc-piperazine was used in all cases. Yields shown represent isolated yields following column chromatography.

The invention has been described in detail with particular reference to preferred embodiments thereof, but it will be understood that variations and modifications can be effected within the spirit and scope of the invention.

What is claimed:

1. A method for forming an optionally substituted 2-aminobenzoxazole compound, said method comprising:
    contacting an optionally substituted 2-aminophenol compound with
    (1) an amine of the formula $NHR^2R^3$, wherein $R^2$ and $R^3$ are each independently selected from H, an optionally substituted alkyl group or an optionally substituted aryl group, or $R^2$ and $R^3$, taken together with the nitrogen atom to which they are attached, form an optionally substituted heterocyclic ring; and
(2) a reactant selected from the group consisting of:
(a) C(OR)$_4$, wherein R represents an alkyl group;
(b) C(OAr)$_4$, wherein Ar represents an aryl group; and
(c) CCl$_2$(OAr)$_2$, wherein Ar represents an aryl group,
in combination with a base;
thereby forming said optionally substituted 2-aminobenzoxazole compound.

2. The method of claim 1 wherein said contacting is carried out in the presence of a solvent.

3. The method of claim 2 wherein said solvent is selected from the group consisting of methanol, ethanol, isopropyl alcohol, acetonitrile, tetrahydrofuran, ethyl acetate, toluene, chloroform, and combinations thereof.

4. The method of claim 3 wherein said solvent further includes an acid.

5. The method of claim 1 wherein R represents a methyl group or an ethyl group.

6. The method of claim 1 wherein Ar represents a phenyl group.

7. The method of claim 1 wherein said contacting is carried out at a temperature of about normal room temperature to about 80° C.

8. The method of claim 1 wherein said base comprises a tertiary amine or an aromatic nitrogen heterocycle.

9. The method of claim 8 wherein said base comprises triethylamine.

10. The method of claim 1 wherein at least one of R$^2$ and R$^3$ comprises an alkyl group.

11. The method of claim 1 wherein R$^2$ and R$^3$ together comprise an alkylene group.

12. The method of claim 1 wherein said amine comprises a primary amine.

13. The method of claim 1 wherein said amine comprises a cycloalkyl secondary amine.

14. The method of claim 1 wherein said amine comprises a heterocyclic secondary amine.

15. The method of claim 14 wherein said heterocyclic secondary amine is N-Boc-piperazine.

16. The method of claim 1 wherein said optionally substituted aryl group in said amine comprises substituents selected from alkyl, aryl, heteroaryl, halo, alkoxy, hydroxyl, acyl, carboalkoxy, carboxy, nitro, and combinations thereof.

17. The method of claim 1 wherein said amine of the formula NHR$^2$R$^3$ is selected from the group consisting of:

18. The method of claim 1 wherein said optionally substituted 2-aminophenol compound is selected from the group consisting of:

19. The method of claim 1 wherein said optionally substituted 2-aminobenzoxazole compound is selected from the group consisting of:

-continued
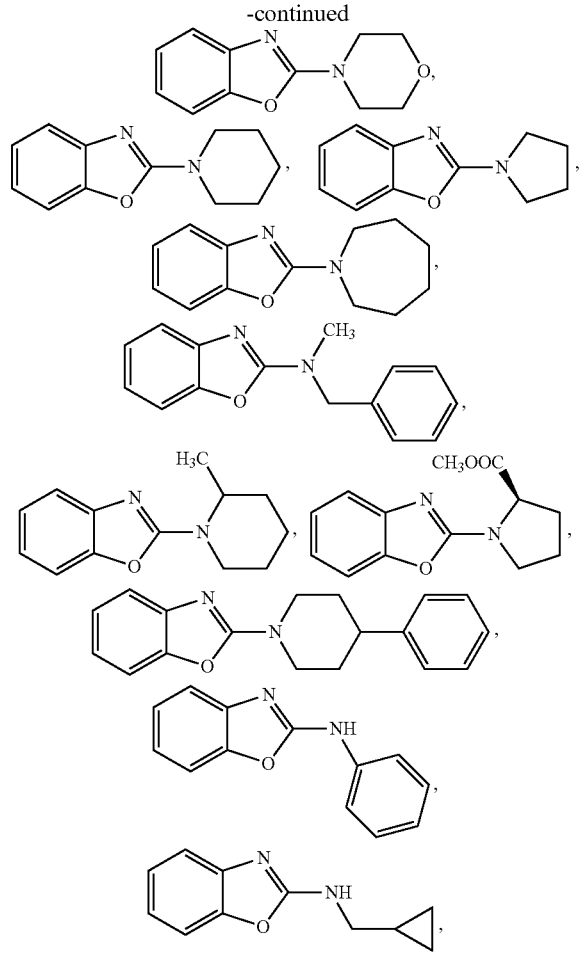
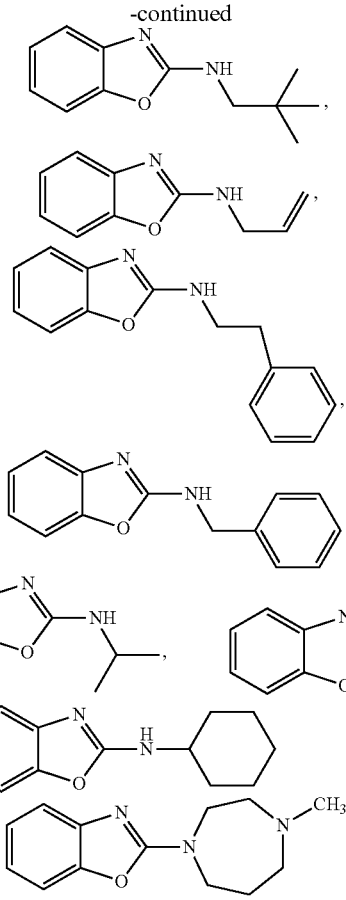
* * * * *